United States Patent [19]

Feijen et al.

[11] Patent Number: 4,526,714
[45] Date of Patent: Jul. 2, 1985

[54] CONJUGATES OF ANTICOAGULANT AND PROTEIN

[75] Inventors: Jan Feijen, Hengelo; Wilhelmus E. Hennink, Enschede, both of Netherlands

[73] Assignee: Cordis Europa N.V., Roden, Netherlands

[21] Appl. No.: 449,248

[22] Filed: Dec. 13, 1982

[51] Int. Cl.³ .............................................. C08B 37/10
[52] U.S. Cl. ............................ 260/112 R; 260/112 B; 260/121; 424/16; 424/36; 424/101; 514/56; 514/2; 514/802; 514/822; 436/524; 536/21
[58] Field of Search ............... 260/112 R, 112 B, 121, 260/122; 424/16, 36, 101, 177, 183, 359; 436/524; 536/21

[56] References Cited

U.S. PATENT DOCUMENTS

| | | | |
|---|---|---|---|
| 3,099,600 | 7/1963 | Toccaceli | 167/74 |
| 4,001,200 | 1/1977 | Bonsen et al. | 260/112 B |
| 4,003,792 | 1/1977 | Mill et al. | 195/63 |
| 4,082,507 | 4/1978 | Sawyer | 8/94.11 |
| 4,326,532 | 4/1982 | Hammar | 424/183 |
| 4,329,383 | 5/1982 | Joh | 424/183 |
| 4,342,739 | 8/1982 | Kakimi et al. | 424/32 |

FOREIGN PATENT DOCUMENTS 2720544 12/1977 Fed. Rep. of Germany .
2318189 2/1977 France .
1515963 7/1975 United Kingdom .

OTHER PUBLICATIONS

Chemical Abstracts, vol. 77, No. 3, Jul. 17, 1972 (Columbus, Ohio) R. V. Yunusov "Complexing of Heparin with Plasma Proteins", Second p. 296, Paragraph 17003r, Vop. Med. Khim 1972, vol. 18, No. 2, pp. 189–191.
Thrombosis Research, vol. 7, 1975, pp. 273–284, Teien et al.

Primary Examiner—Morton Foelak
Assistant Examiner—Nathan M. Nutter
Attorney, Agent, or Firm—Lockwood, Alex, Fitzgibbon & Cummings

[57] ABSTRACT

Conjugates are provided which are covalently bonded conjugates of an anticoagulant and protein that are prepared in the presence of a coupling agent that forms amide linkages between the anticoagulant and the protein. Such amide linking coupling agents exclude highly toxic coupling agents such as CNBr. These conjugates are useful for enhancing the blood compatibility of certain surfaces of a prosthetic device, a surgical apparatus, or an extra-corporeal medical device.

16 Claims, 7 Drawing Figures

FIG.5

CONJUGATES OF ANTICOAGULANT AND PROTEIN

BACKGROUND AND DESCRIPTION OF THE INVENTION

The invention relates to a process for the preparation of a conjugate of an anticoagulant such as heparin to a water soluble protein, typically human protein, by coupling the heparin to the protein in an aqueous medium and in the presence of a coupling agent.

In the article "Heparin Coupled to Albumin, Dextran and Ficoll; Influence on Blood Coagulation and Platelets and in vivo Duration", Thrombosis Research 7 (1975) 273–284, A. N. Teien et al, the authors report upon an investigation carried out by them which indicates that a heparin-albumin complex possesses anticoagulation and aggregation effects equal to those of free heparin. The heparin-albumin complex involved in their investigation was prepared by adding CNBr to a solution containing dextran, effecting an activation of the dextran in order to bridge heparin to the albumin, after which the whole is mixed with an aqueous solution of heparin and albumin. The heparin-albumin complexes so obtained are then lyophilized and stored in Veronal buffer and are incorporated in a stock solution containing 16 mg heparin per $cm^3$, which assumes complete recovery of heparin. The complexes thus formed possess a molecular weight distribution due to, inter alia, the heterogenity of the commercial heparin preparations, which also exhibit a distribution of molecular weights. Using CNBr in such a process is undesirable because of the very high toxicity of CNBr. Also, using CNBr in this maanner does not form covalent amide linkages.

An object of the invention is an improved process for the preparation of conjugates of heparin to a human protein, such conjugates being suitable to treat a material surface or substrate for the improvement of its blood compatibility, particularly regarding the prevention of blood coagulation and damage of blood components. When a substrate is coated with such a conjugate, its blood compatibility is improved, and the conjugates of this invention are advantageously applied to artificial organs, implants, catheters, and other medical prostheses which are contacted with blood.

According to this invention, the coupling agent for forming the conjugates should form amide linkages between an anticoagulant such as heparin and protein. The preferred coupling agent in this regard is 1-ethyl-3-dimethylaminopropyl carbodiimide (or EDC).

EDC has been found to provide the best and most reproducible results, particularly when EDC is applied as the coupling agent and when the coupling is carried out in an aqueous solution of heparin and the protein. Within the process according to the invention, the coupling reaction between the carboxyl groups present in heparin and $\epsilon\text{-NH}_2$-groups of lysine residues present in the protein, is a direct coupling between these groups, a heparin intermediate product being formed wherein the carboxyl groups are activated by EDC to active ester groups, which activated carboxyl groups are in turn reactive towards the amino groups of the protein.

In a further elaboration of the process according to the invention that utilizes EDC, the heparin and the protein are each provided dissolved in water; the pH of the solution is adjusted to a value of not higher than 5.5, preferably between about 5.0 and 5.5; an aqueous solution of EDC is added batchwise while maintaining the pH on a level of not higher than 5.5; the coupling reaction is carried out in the reaction mixture while agitating it; and the heparin-protein conjugate is recovered from the reaction mixture.

Normally, the reaction is carried out at room temperature. However, higher temperatures may be applied, for example body temperature, and up to the denaturation temperature of the applied protein, typically up to about 60 degrees centigrade. Generally, the concentration of the components heparin and protein to be coupled can be varied greatly in the aqueous solutions, and the ratio of these components to each other in the conjugate may be varied up to a certain level by varying the weight ratio of heparin to protein.

With further reference to the pH values of this process, when the coupling reaction according to this invention uses EDC, if there is a failure to adjust and maintain the pH-value at or below a pH value of about 5.5, the rate of the reaction of heparin with EDC is very low because the concentration of the protonated carbodiimide groups of EDC is too low. Coupling agents other than EDC may exhibit different upper pH limits.

If the pH is too low, there are two undesirable results; denaturation of the protein takes place, and the sulphamate groups in the heparin will be transformed into amino groups. Therefore, it is preferred that the pH of the reaction mixture is adjusted to and maintained at a value that is equal to or greater than 5.0.

When heparin-protein conjugates are formed according to the invention, the composition of the components to be coupled may be at various weight ratios during the coupling reaction. A typical preferred weight ratio for the amounts of heparin and protein used in the process is such that the mol ratio of heparin to protein in the conjugate is about 1 to 1, although other weight ratios may be utilized so that heparin-protein conjugates are obtained at a different mol ratio. One characteristic to be avoided in this regard is to attempt to couple excessive heparin molecules onto the protein to the extent that the conjugate is overly hydrophilic and will not adsorb onto hydrophobic substrates. Heparin does not readily adsorb onto hydrophobic substrates, while a protein such as albumin does so readily adsorb, and typically a mol ratio of heparin to albumin above 3 to 1 should be avoided.

Regarding the protein which is to be used as the reaction component, and which is a generally water soluble human protein, such may be a water soluble protein, suitable for coupling and appearing in blood, for example albumin, fibrinogen, γ-globulin, and the like. Albumin is preferred because, of the human proteins, albumin has the highest concentration in human blood. Moreover, albumin exerts a strengthened inhibiting effect relative to the adhesion of blood platelets. These proteins may be used as such or in crosslinked form, for example by crosslinking with an aldehyde, for example glutaraldehyde. Dependent on the protein component used, one should always experimentally determine the desired pH of the reaction mixture, particularly from the point of view of avoiding undesirable denaturation of the particular protein used.

With regard to the anticoagulant, for example, heparin fractions may be used which are separated from heparin by fractionating it on the basis of difference in molecular weight and/or affinity relative to anti-thrombin III. Because it is generally known that, by fractionating heparin with immobilized anti-thrombin III, heparin fractions with high and low affinity may be obtained, the use of fractionated heparin offers the possibility to control the anti-thrombogenic activity of the heparin-protein conjugate.

After the coupling reaction has taken place, the reaction mixture contains not only the desired covalently bonded heparin-protein conjugate, but also free, that is to say non-reacted, protein and heparin. To isolate the conjugate from the reaction mixture, after optionally having subjected the mixture to a prepurification, for example by dialysing it to remove superfluous EDC, the mixture preferably is passed over a first sorption agent, which sorbs the heparin-protein conjugate, free protein and free heparin. Whereupon, by elution with eluent of increasing ionic strength, it is possible to first desorb the free protein and subsequently the heparinous compounds, and the eluate which contain the heparinous compounds are preferably then passed over a second sorption agent, by elution of which one separately desorbs the free heparin and the heparin-protein conjugate, respectively, and isolates the heparin-protein conjugate. Preferably such a first sorption agent would be an anion exchange synthetic resin material, and the second sorption agent would be a material with different affinity relative to the heparinous compounds.

The invention also relates to a process for the improvement of the blood compatibility of a material surface or substrate by coating it with heparin or with heparin analogues as is generally discussed in "Artificial Organs, Proceedings of a Seminar on the Clinical Applications of Membrane Oxygenators and Sorbent Based Systems", MacMillan Press Ltd., 1977. In chapter 26 thereof, at pages 235–247, J. Feijen under the title "Thrombogenisis Caused by Blood-Foreign Surface Interaction" discusses the developments in the field of the blood compatibility of material surfaces, particularly regarding the occurring protein adsorption, adhesion of blood platelets and activation of intrinsic coagulation.

Within the framework of improving the blood compatibility of a material surface by coating it with an anticoagulant such as heparin or heparin analogues, the invention is characterized in that a heparin/non-crosslinked conjugate, prepared by the process according to the invention described hereinabove, is adsorbed to a hydrophobic or hydrophilic material surface, particularly to a hydrophobic material surface, in which case the protein moiety will be directed to the material surface and the heparin moiety in the blood.

In some applications and aspects of this invention, it is desired to minimize the desorption of the coated anticoagulant-protein conjugate by exchange with other plasma proteins. Such can be accomplished by crosslinking the protein moiety of the conjugate, typically after the conjugate has been formed and coated onto the material surface or substrate.

Apart from adsorption for the improvement of the blood compatability of a material surface by coating it with heparin or heparin analogues, it is also possible to prepare and provide anticoagulant protein conjugates according to the present invention which are chemically attached to the material surface or substrate. In this instance, the protein is considered as a so-called "spacer" group, while it is also possible to effect an eventual crosslink-reaction of the protein moiety after the material surface is coated with the heparin-protein conjugate having a non-crosslinked protein moiety.

The improvement of the blood compatibility of a material surface by coating it with an anticoagulant such as heparin or heparin analogues may also be effected by providing the material surface with a crosslinked protein layer, whereupon heparin is coupled to the protein by the application of EDC as the coupling agent. In the coating obtained with this embodiment of the invention, the coupling takes place via the amino groups of the protein, and the protein may also be considered as a "spacer" group between the material surface and the heparin.

Depending upon the particular aspect of this invention needed to provide a desired result, the conjugates may be generally firmly attached to the substrate surface, usually in association with a cross-linking operation, or they may be only adsorbed thereto. Adsorbed conjugates will exhibit desorption to the extent that the conjugates will become generally released such that the conjugates will provide anticoagulation properties to the blood flowing past the substrate. In effect, this aspect of the invention provides controlled release of anticoagulant properties, which can be valuable in connection with treatments using extra-corporeal devices such as catheters, in connection with pretreatment of prosthetic devices such as artificial blood vessels where enhanced tissue ingrowth is very advantageous, or in connection with surgical apparatus such as oxygenators where only temporary anticoagulation is needed. The rate and extent of such desorption or controlled release of conjugates will depend upon the particular conjugate, upon the hydrophobic or hydrophilic nature of the substrate being coated, and upon the rate of blood flow that contacts the substrate.

The invention will be further explained by the following examples, in which albumin is applied as the protein component.

EXAMPLE I (a) Preparation

In this example, the process is carried out at room temperature. 770 mg of heparin and 2590 mg of human serumalbumin were dissolved in 39 $cm^3$ of water. By means of 1.0N HCl, the pH of this solution was adjusted to between 5.0 and 5.5. During the addition, a white-flaky precipitate is generated, which is dissolved after about 30 minutes. Thereupon, incremental batches of 1 $cm^3$ EDC-solution (concentration 32.5 $mg/cm^3$) were added. Eight incremental batches were added at 30-minute intervals. As necessary, the pH was maintained at between 5.0 and 5.5 by the addition of 1.0N HCl or 1.0N NaOH. After all of the EDC was added, the pH of the solution was adjusted to 7.5 by means of 1.0N NaOH, whereupon the solution was agitated during 20 hours at room temperature. Thereafter, the solution was dialyzed for 2 hours against a 25 mmol tris/HCl solution (pH 7.5) to remove superfluous EDC.

(b) Isolation of the conjugate

Figure 1:
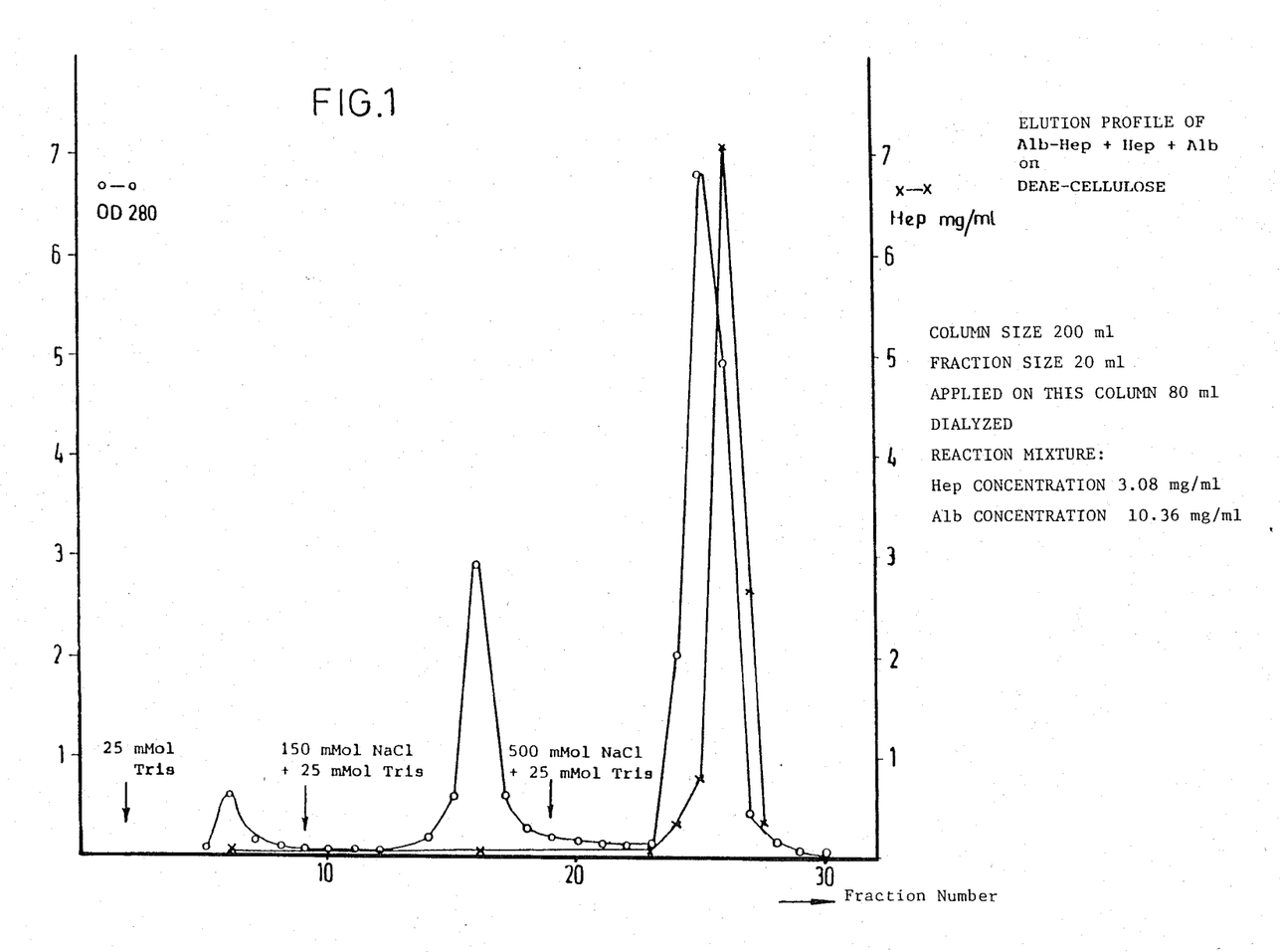
Figure 2:
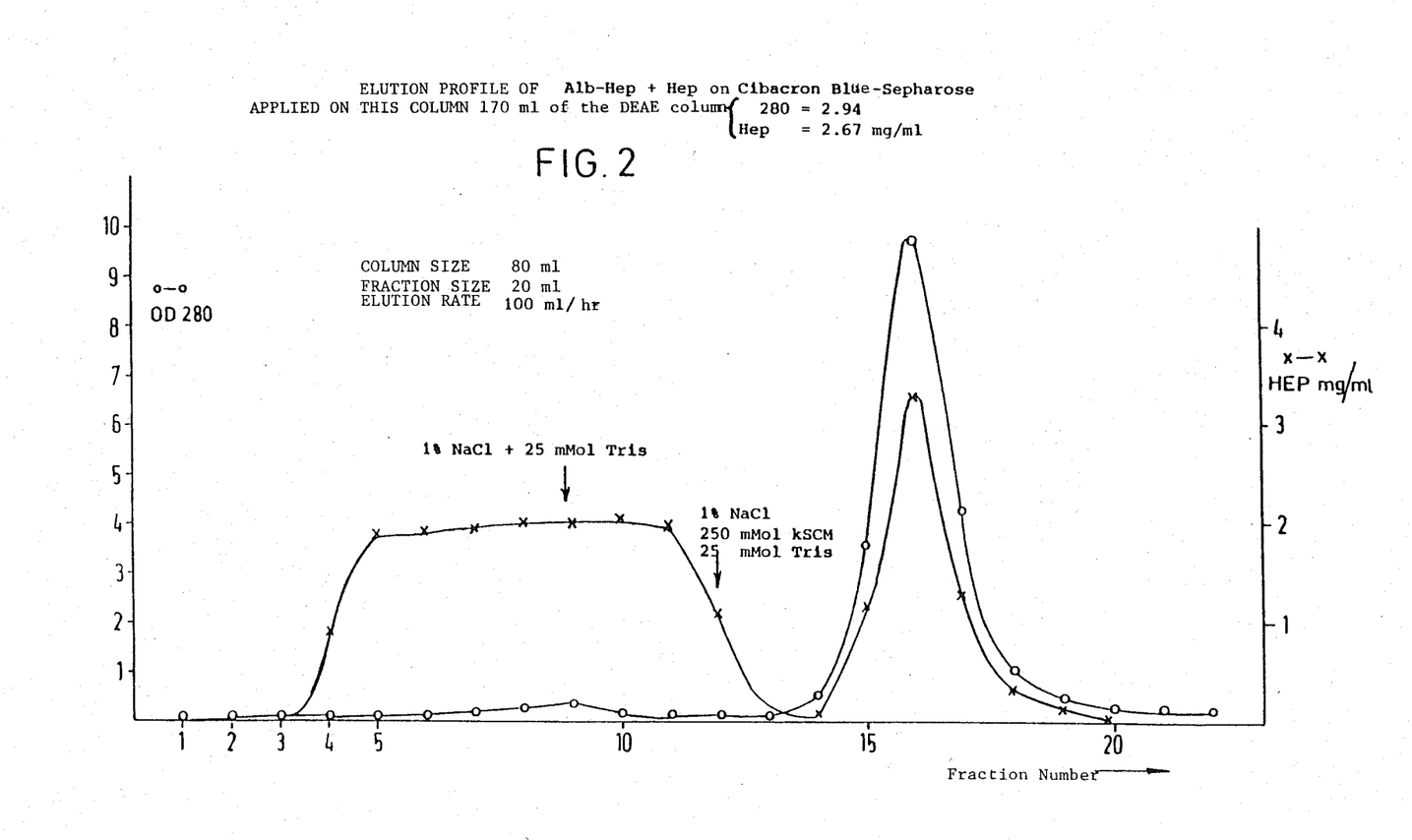

In addition to the desired albumin-heparin conjugate, the reaction mixture also contained albumin and heparin which had not yet reacted. For the separation of these free components, use was made of an anion exchange column and an affinity column, i.e. a column provided with diethylaminoethyl-cellulose (DEAE-cellulose), followed by a column provided with Cibracron Blue Sepharose (CB-Sepharose). The dialyzed reaction mixture obtained in this manner was passed over a DEAE-cellulose column (5 mg material/cm³ gel) which was in equilibrium with 25 mmol tris/HCl at pH=7.5. Then, the column was eluted with one column volume of 25 mmol tris/HCl (pH 7.5). Thereupon the column was eluted with 1.5-2 times the column volume 150 mmol NaCl+25 mmol tris/HCl (pH 7.5). At this step the ionic strength of the elution liquid was such that the "free" albumin which had not reacted was being separated from the column and eluted. Next, the DEAE-column was eluted with 1.5-2 times the column volume 500 mmol NaCl+25 mmol tris/HCl (pH 7.5). At this ionic strength the heparin-albumin conjugate as well as the non-reacted "free" heparin was separated from the column. The fractions which were received through elution of the column with the solution containing 500 mmol NaCl, and which had an optical density at 280 nm ($\lambda_{max}$albumin))>0.2, were combined and used for further purification with CB-Sepharose. The elution pattern of the DEAE-separation, as described above, is shown in FIG. 1. The CB-Sepharose column was equilibrated with a 1% NaCl and 25 mmol tris/HCl (pH 7.5) solution, whereupon the combined fractions of the DEAE-column were passed over the CB-Sepharose column. To remove the "free" heparin present in the solution, the column was eluted with 1 times the column volume 1% NaCl and 25 mmol tris/HCl (pH 7.5) solution. Thereupon, the albumin-heparin conjugate was eluted from the CB-column by means of a 1% NaCl+25 mmol tris/HCl (pH 7.5)+250 mmol KSCN solution. The fractions having an optical density at 280 nm>0.2 were combined, exhaustively dialyzed against water and finally freeze dried. The elution pattern of a CB-Sepharose separation as described above is shown in FIG. 2. All chromatographic experiments were carried out at a temperature of 4° C.

EXAMPLE II

Anti-thrombogenic activity of heparin-albumin conjugates

A heparin-albumin conjugate was prepared using the process described in Example I, starting with nonfractionated heparin.

Figure 3:
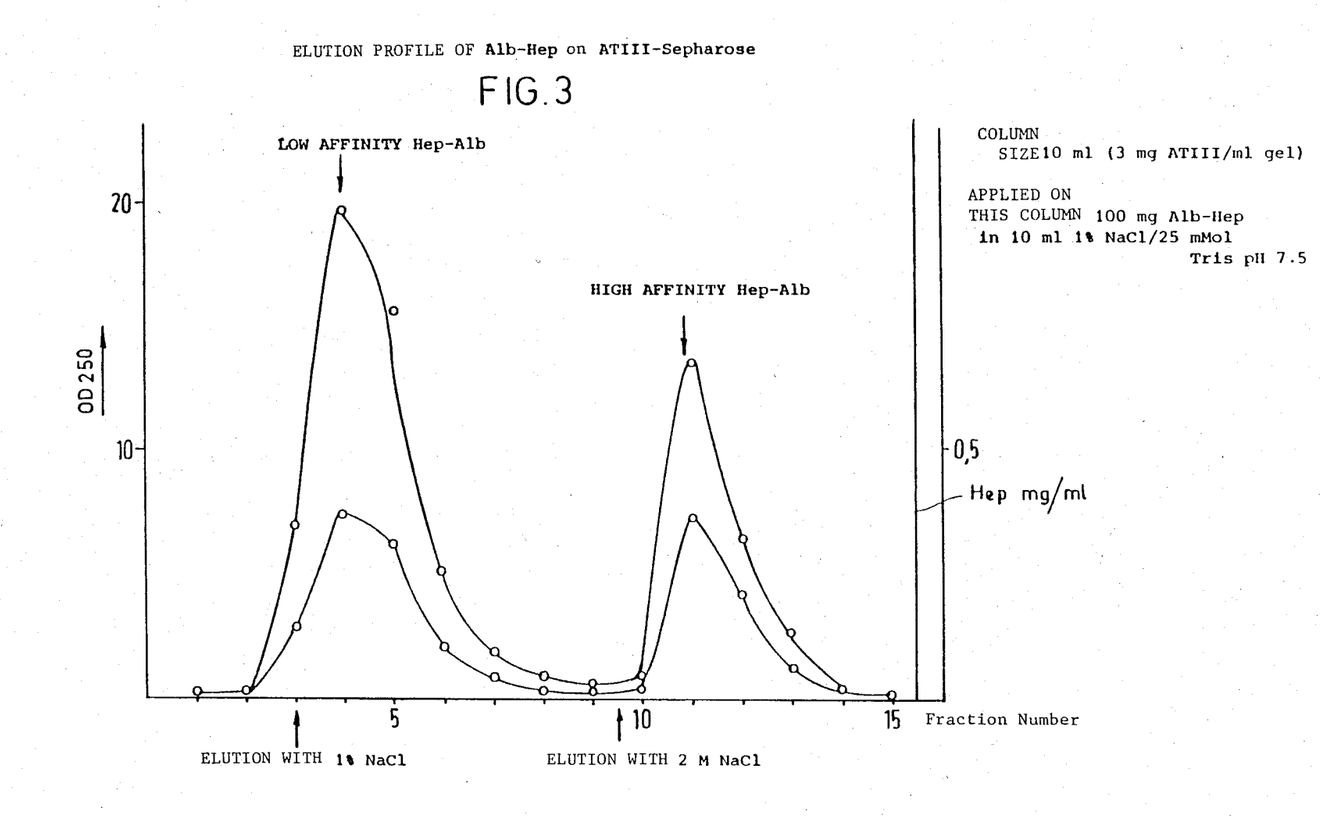
Figure 4:
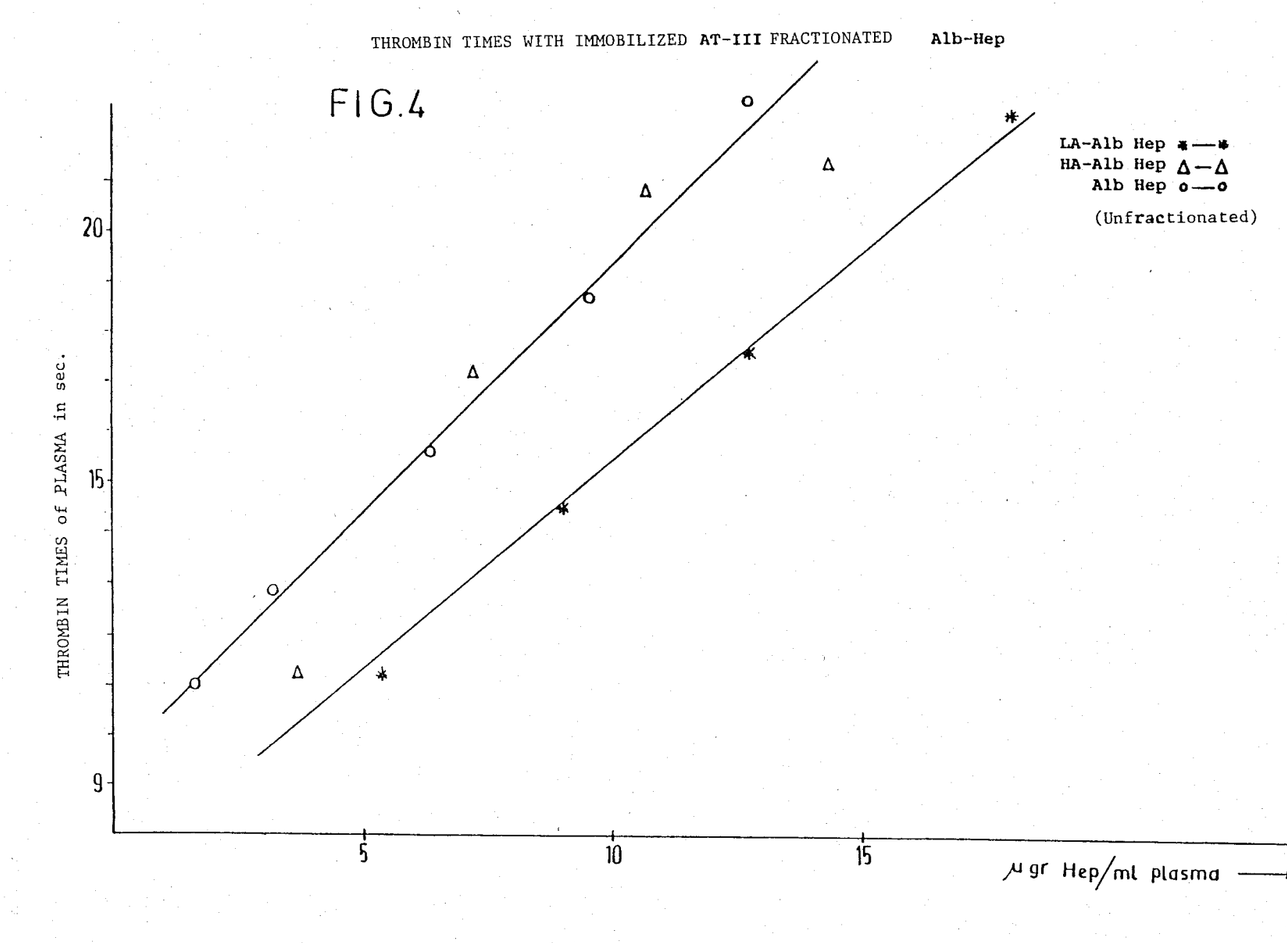
Figure 5:
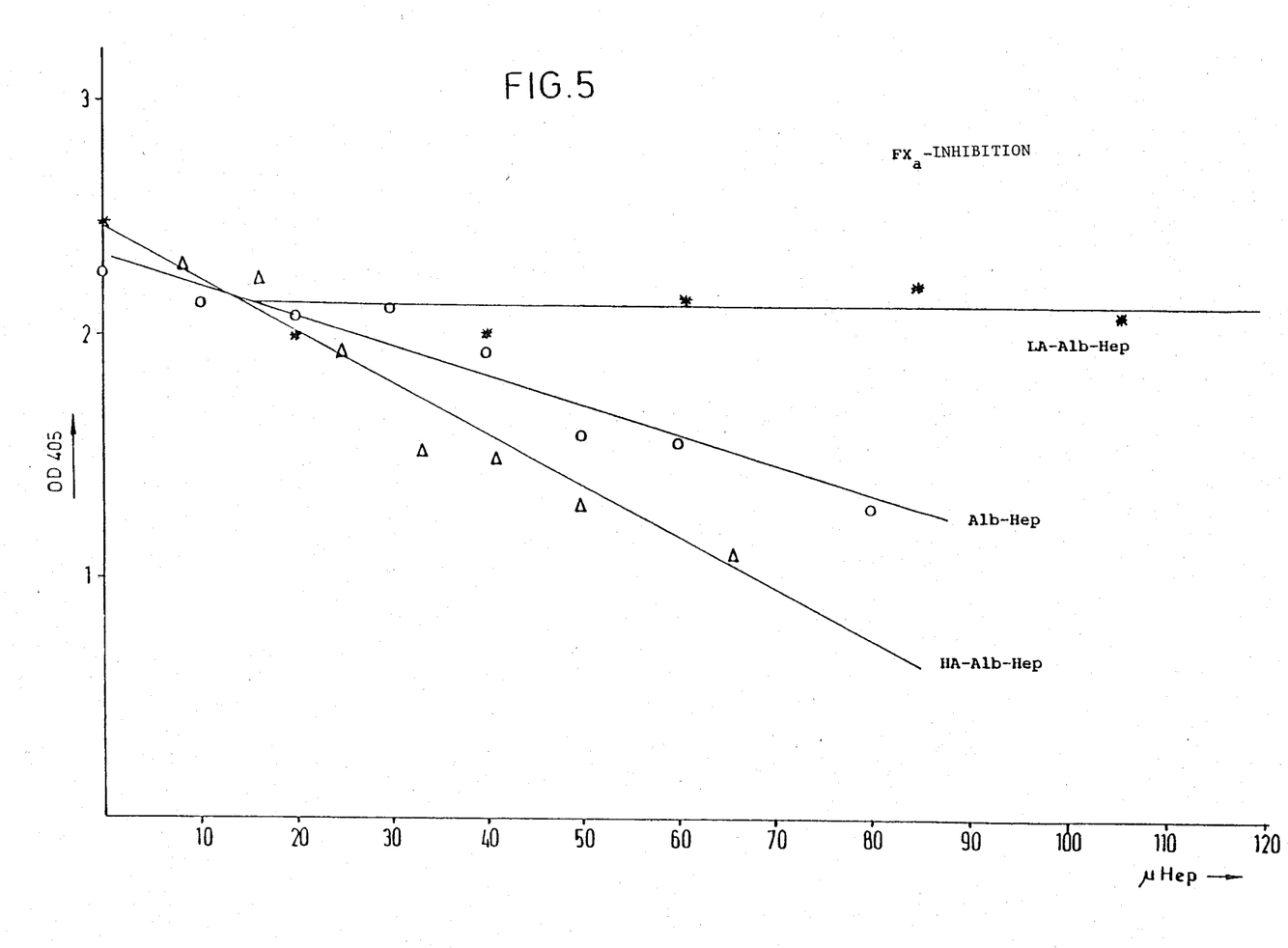

The conjugate prepared according to Example I was passed over an anti-thrombin III Sepharose-column. The elution pattern of this conjugate showed two fractions (FIG. 3); both fractions were measured on thrombininactivation (FIG. 4) and on factor Xa inactivation (FIG. 5). The results show that the several fractions differ in anti-coagulant activity.

Figure 6:
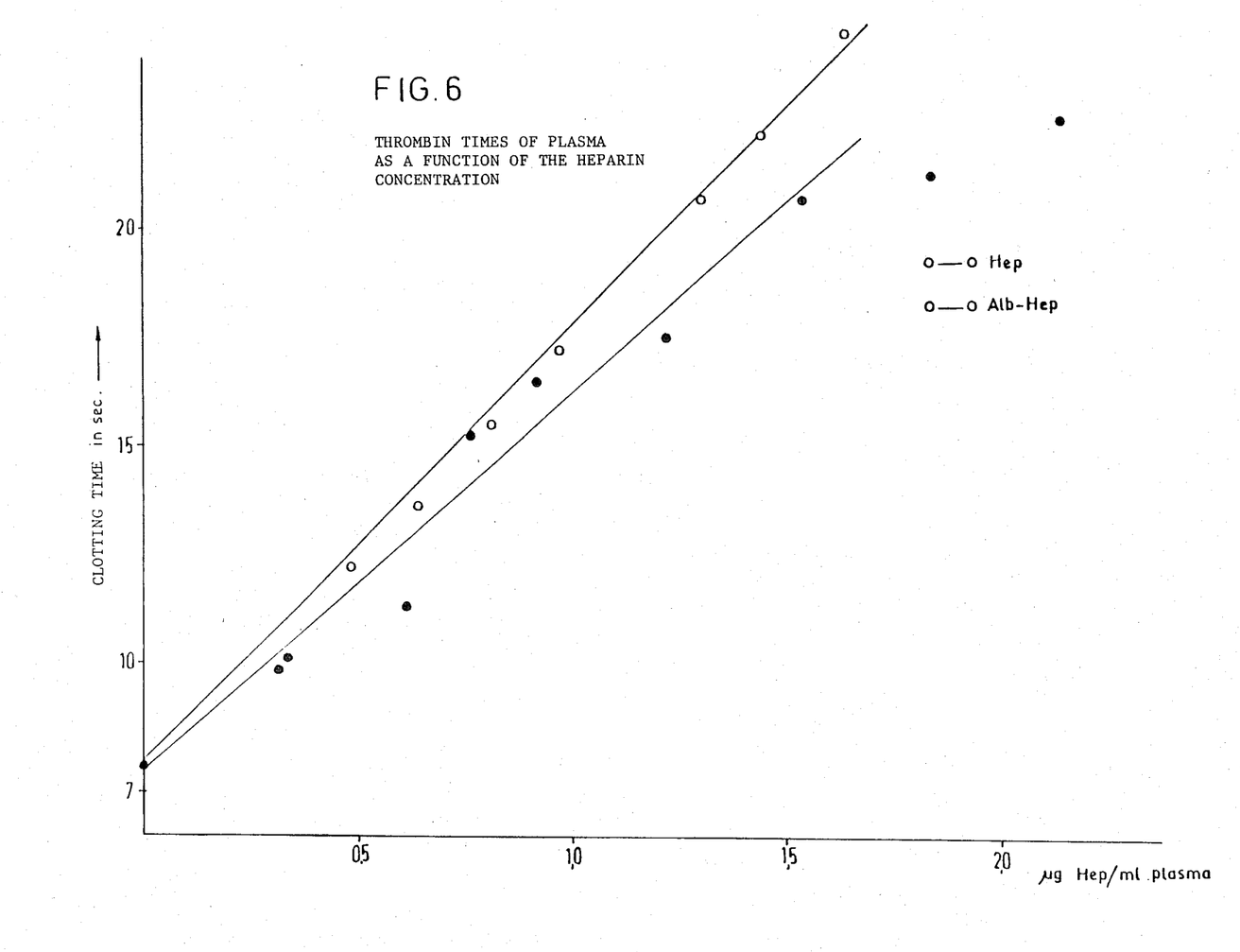
Figure 7:
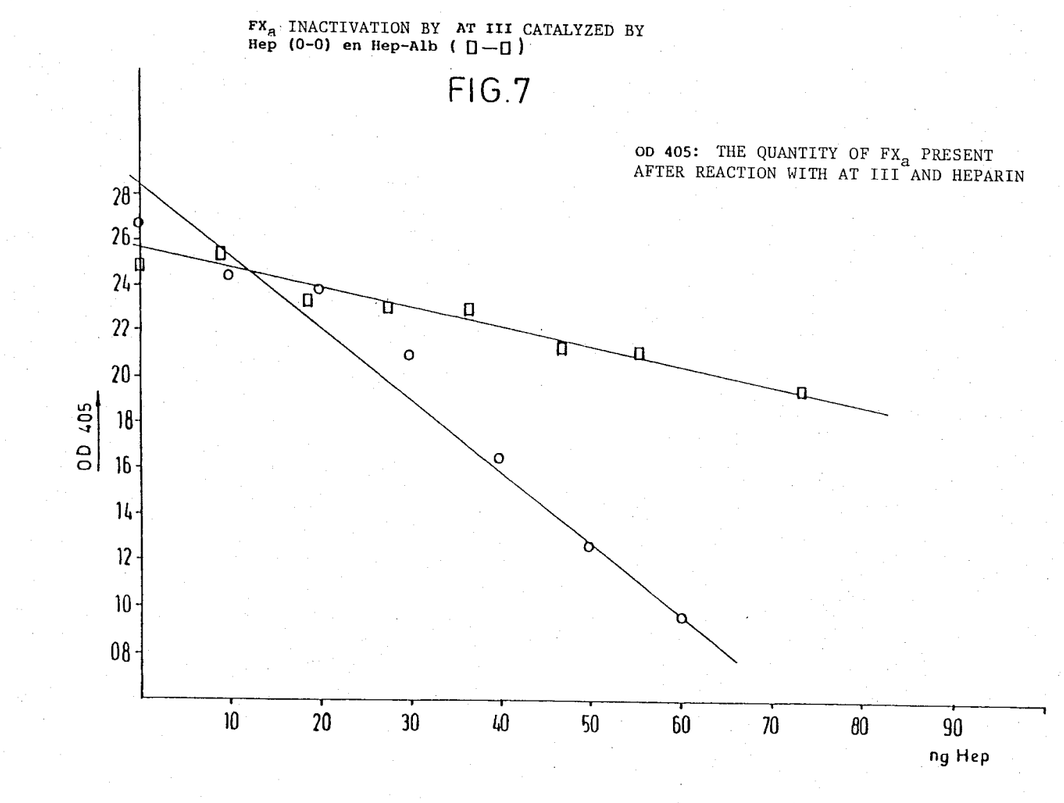

Moreover, the conjugate prepared according to Example I, on the basis of both inactivation experiments, was measured and compared with heparin, which was used for the synthesis of the heparin-albumin conjugate. The results thereof in FIG. 6 and in FIG. 7 show that the conjugate has working properties comparable to those of the heparin that was used for the synthesis of the conjugate.

We claim:

1. A process for the improvement of compatibility between blood and a substrate, the process including coating the substrate with an anticoagulant material, wherein the process comprises adsorbing a protein-anticoagulant conjugate to said substrate, said substrate being a hydrophobic material or a hydrophilic material, said protein of the protein-anticoagulant conjugate being a water soluble protein that is non-crosslinked when adsorbed onto said substrate, and said protein-anticoagulant conjugate is prepared according to a process that includes coupling said anticoagulant to said water soluble, non-crosslinked protein within an aqueous medium and in the presence of a coupling agent and providing an anticoagulant-protein conjugate by using a coupling agent that is an amide bond forming agent to form an amide linkage between said anticoagulant and said protein.

2. The process according to claim 1, wherein the process further includes intermolecular crosslinking of the protein.

3. The process according to claim 1, wherein said substrate is a hydrophobic material.

4. The process according to claim 1, wherein said anticoagulant is a heparinous material, said conjugate is a water soluble human protein-heparin conjugate, and said coupling agent is 1-ethyl-3-dimethylaminopropyl carbodiimide.

5. The process according to claim 4, wherein the process further includes intermolecular crosslinking of the protein.

6. The process according to claim 4, wherein said substrate is a hydrophobic material.

7. A process for the improvement of compatibility between blood and a substrate, the process including coating the substrate with an anticoagulant material, wherein the process comprises chemically attaching a protein-anticoagulant conjugate having been prepared according to a process that includes selecting a water soluble human protein as said protein, coupling said anticoagulant to said protein within an aqueous medium and in the presence of a coupling agent and providing an anticoagulant-protein conjugate by using a coupling agent that is an amide bond forming agent to form an amide linkage between said anticoagulant and said protein, and the protein of said protein-anticoagulant conjugate is non-crosslinked and soluble when chemically attached to said substrate.

8. The process according to claim 7, wherein the process further includes intermolecular crosslinking of the protein.

9. The process according to claim 7, wherein said anticoagulant is a heparinous material, said conjugate is a protein-heparin conjugate, and said coupling agent is 1-ethyl-3-dimethylaminopropyl carbodiimide.

10. The process according to claim 9, wherein the process further includes intermolecular crosslinking of the protein.

11. A process for the improvement of compatibility between blood and a substrate, the process including coating the substrate with anticoagulant material, wherein the process comprises coating the substrate with a protein component, said protein component being a non-crosslinked protein, wherein said protein component is a water soluble human protein that is coupled with anticoagulant by a procedure utilizing an amide bond forming agent as a coupling agent, said procedure being such that the coupled protein and anticoagulant is substantially non-crosslinked when coated onto the substrate.

12. The process according to claim 11, wherein said protein component is albumin and the anticoagulant is a heparinous material.

13. The process according to claim 11, wherein said anticoagulant is heparinous material, and wherein said protein component is coupled with heparin by a procedure utilizing 1-ethyl-3-dimethylaminopropyl carbodiimide as the coupling agent.

14. A process for the improvement of compatibility between blood and a substrate, the process including coating the substrate with anticoagulant material, wherein the process comprises covalently linking a protein component to a substrate, said protein component being a non-crosslinked protein, wherein said protein component is a water soluble human protein that is coupled with anticoagulant by a procedure utilizing an amide bond forming agent as a coupling reagent, said procedure being such that the coupled protein and anticoagulant is substantially non-crosslinked when coated onto the substrate.

15. The process according to claim 13, wherein said protein component is albumin and the anticoagulant is a heparinous material.

16. The process according to claim 13, wherein said anticoagulant is a heparinous material, and wherein said protein component is coupled with heparin by a procedure utilizing 1-ethyl-3-dimethylaminopropyl carbodiimide as the coupling agent.

* * * * *